(12) United States Patent
Borillo et al.

(10) Patent No.: US 7,169,164 B2
(45) Date of Patent: Jan. 30, 2007

(54) APPARATUS FOR IMPLANTING DEVICES IN ATRIAL APPENDAGES

(75) Inventors: Thomas E Borillo, Plymouth, MN (US); Gregg S Sutton, Maple Grove, MN (US)

(73) Assignee: Atritech, Inc., Plymouth, MN (US)

( * ) Notice: Subject to any disclaimer, the term of this patent is extended or adjusted under 35 U.S.C. 154(b) by 355 days.

(21) Appl. No.: 09/960,749

(22) Filed: Sep. 21, 2001

(65) Prior Publication Data

US 2002/0035374 A1    Mar. 21, 2002

Related U.S. Application Data

(60) Provisional application No. 60/234,111, filed on Sep. 21, 2000.

(51) Int. Cl.
*A61B 17/08* (2006.01)

(52) U.S. Cl. .......................... 606/200; 606/213

(58) Field of Classification Search ............... 606/151, 606/157, 158, 191, 192, 194, 195, 198, 200, 606/213

See application file for complete search history.

(56) References Cited

U.S. PATENT DOCUMENTS 178,283 A    6/1876  French (Continued)

FOREIGN PATENT DOCUMENTS

CN    2105968 U    6/1992

(Continued)

OTHER PUBLICATIONS

Cragg et al., "Nonsurgical Placement of Arterial Endoprosthesis: A New Technique Using Nitinol Wire," *Radiology* vol. 147, No. 1, pp. 261-263, Apr. 1983.

(Continued)

*Primary Examiner*—Anhtuan T. Nguyen
*Assistant Examiner*—Jessica R. Baxter
(74) *Attorney, Agent, or Firm*—Fish & Neave IP Group Ropes & Gray LLP

(57) ABSTRACT

The invention provides a delivery system for placing devices in atrial appendages. The system includes a catheterization apparatus having a tubular structure with one or more nested tubes, wires, and shafts. The tubes establish a passageway for moving a device through a body's vasculature and heart into an atrial appendage. An expandable positioning guide is disposed on the distal end of a tube passing through the apparatus. The positioning guide is expanded in situ to engage atrial wall surfaces proximate to the atrial appendage for mechanical support. The deployed positioning guide mechanically stabilizes the device delivery passageway. A shaft passing through the tubes transports the device through the passageway to the atrial appendage.

The system includes catheterization apparatus for transseptal delivery of the devices. An outer tube or sheath in the apparatus is used to penetrate and traverse the septum. An expandable securement device is disposed toward an end of the sheath. The securement device is expanded in situ to engage surface portions of the traversed septum to restrain further inadvertent movement of the septum-traversing sheath.

13 Claims, 3 Drawing Sheets

U.S. PATENT DOCUMENTS

| | | | |
|---|---|---|---|
| 1,967,318 A | 7/1934 | Monahan | 128/227 |
| 3,844,302 A | 10/1974 | Klein | 135/26 |
| 3,874,388 A | 4/1975 | King et al. | 128/334 R |
| 4,007,743 A | 2/1977 | Blake | 128/334 |
| 4,341,218 A | 7/1982 | Ü | 128/325 |
| 4,585,000 A | 4/1986 | Hershenson | 128/345 |
| 4,603,693 A | 8/1986 | Conta et al. | 128/305 |
| 4,665,906 A | 5/1987 | Jervis | 128/92 |
| 4,710,192 A | 12/1987 | Liotta et al. | 623/1 |
| 4,753,637 A * | 6/1988 | Horneffer | 606/194 |
| 4,836,204 A * | 6/1989 | Landymore et al. | 606/195 |
| 4,917,089 A | 4/1990 | Sideris | 606/215 |
| 4,921,484 A | 5/1990 | Hillstead | 604/104 |
| 5,037,810 A | 8/1991 | Sabila, Jr. | 514/56 |
| 5,041,090 A | 8/1991 | Scheglov et al. | 604/101 |
| 5,041,093 A | 8/1991 | Chu | 604/104 |
| 5,042,707 A | 8/1991 | Taheri | 606/213 |
| 5,053,009 A | 10/1991 | Herzberg | 604/104 |
| 5,064,435 A | 11/1991 | Porter | 623/12 |
| 5,078,736 A | 1/1992 | Behl | 623/1 |
| 5,108,420 A | 4/1992 | Marks | 606/213 |
| 5,171,259 A | 12/1992 | Inoue | 606/213 |
| 5,176,692 A | 1/1993 | Wilk et al. | 606/151 |
| 5,192,301 A | 3/1993 | Kamiya et al. | 606/213 |
| 5,256,146 A | 10/1993 | Ensminger et al. | 604/104 |
| 5,258,042 A | 11/1993 | Mehta | 623/66 |
| 5,284,488 A | 2/1994 | Sideris | 606/213 |
| 5,306,234 A | 4/1994 | Johnson | 604/49 |
| 5,312,341 A * | 5/1994 | Turi | 606/194 |
| 5,334,217 A | 8/1994 | Das | 606/213 |
| 5,350,399 A | 9/1994 | Erlebacher et al. | 606/213 |
| 5,353,784 A | 10/1994 | Nady-Mohamed | 120/20 |
| 5,370,657 A | 12/1994 | Irie | 606/200 |
| 5,375,612 A | 12/1994 | Cottenceau et al. | 128/899 |
| 5,417,699 A | 5/1995 | Klein et al. | 606/144 |
| 5,421,832 A | 6/1995 | Lefebvre | 604/53 |
| 5,425,744 A | 6/1995 | Fagan et al. | 606/213 |
| 5,433,727 A | 7/1995 | Sideris | 606/213 |
| 5,443,454 A | 8/1995 | Tanabe et al. | 606/264 |
| 5,451,235 A | 9/1995 | Lock et al. | 606/213 |
| 5,464,408 A | 11/1995 | Duc | 606/108 |
| 5,469,867 A | 11/1995 | Schmitt | 128/898 |
| 5,490,856 A | 2/1996 | Person et al. | 606/139 |
| 5,522,822 A | 6/1996 | Phelps et al. | 606/151 |
| 5,522,836 A | 6/1996 | Palermo | 606/200 |
| 5,527,322 A | 6/1996 | Klein et al. | 606/144 |
| 5,527,338 A | 6/1996 | Purdy | 606/200 |
| 5,545,214 A * | 8/1996 | Stevens | 606/191 |
| 5,591,196 A | 1/1997 | Marin et al. | 606/198 |
| 5,614,204 A | 3/1997 | Cochrum | 424/423 |
| 5,634,936 A | 6/1997 | Linden et al. | 606/213 |
| 5,634,942 A | 6/1997 | Chevillon et al. | 623/1 |
| 5,637,097 A | 6/1997 | Yoon | 604/174 |
| 5,643,292 A | 7/1997 | Hart | 606/144 |
| 5,649,953 A | 7/1997 | Lefebvre | 606/200 |
| 5,655,548 A * | 8/1997 | Nelson et al. | 128/898 |
| 5,662,671 A | 9/1997 | Barbut et al. | 606/170 |
| 5,669,933 A | 9/1997 | Simon et al. | 600/200 |
| 5,681,347 A | 10/1997 | Cathcart et al. | 606/200 |
| 5,690,671 A | 11/1997 | McGurk et al. | 606/200 |
| 5,693,067 A | 12/1997 | Purdy | 606/200 |
| 5,695,525 A | 12/1997 | Mulhauser et al. | 623/11 |
| 5,702,421 A | 12/1997 | Schneidt | 606/213 |
| 5,709,224 A | 1/1998 | Behl et al. | 128/898 |
| 5,709,707 A | 1/1998 | Lock et al. | 606/213 |
| 5,725,552 A | 3/1998 | Kotula et al. | 606/213 |
| 5,725,568 A | 3/1998 | Hastings | 623/1 |
| 5,733,294 A | 3/1998 | Forber et al. | 606/151 |
| 5,735,290 A | 4/1998 | Sterman et al. | 128/898 |
| 5,749,883 A | 5/1998 | Halpern | 606/159 |
| 5,749,894 A | 5/1998 | Engelson | 606/213 |
| 5,766,219 A | 6/1998 | Horton | 606/191 |
| 5,769,816 A | 6/1998 | Barbut et al. | 604/49 |
| 5,776,097 A | 7/1998 | Massoud | 604/49 |
| 5,782,860 A | 7/1998 | Epstein et al. | 606/213 |
| 5,797,960 A * | 8/1998 | Stevens et al. | 606/213 |
| 5,810,874 A | 9/1998 | Lefebvre | 606/200 |
| 5,823,198 A | 10/1998 | Jones et al. | 128/899 |
| 5,830,228 A | 11/1998 | Knapp et al. | 606/195 |
| 5,836,913 A | 11/1998 | Orth et al. | 604/107 |
| 5,836,968 A | 11/1998 | Simon et al. | 606/200 |
| 5,846,260 A | 12/1998 | Maahs | 606/200 |
| 5,846,261 A | 12/1998 | Kotula et al. | 606/213 |
| 5,849,005 A | 12/1998 | Garrison et al. | 606/1 |
| 5,851,232 A | 12/1998 | Lois | 623/1 |
| 5,855,597 A | 1/1999 | Jayaraman | 623/1 |
| 5,865,791 A | 2/1999 | Whayne et al. | 604/49 |
| 5,865,802 A | 2/1999 | Yoon et al. | 604/104 |
| 5,868,708 A | 2/1999 | Hart et al. | 604/104 |
| 5,876,367 A | 3/1999 | Kaganov et al. | 604/8 |
| 5,882,340 A | 3/1999 | Yoon | 604/164 |
| 5,885,258 A | 3/1999 | Sachdeva et al. | 604/281 |
| 5,895,399 A | 4/1999 | Barbut et al. | 606/159 |
| 5,904,703 A | 5/1999 | Gilson | 606/213 |
| 5,906,207 A | 5/1999 | Shen | 128/898 |
| 5,910,154 A | 6/1999 | Tsugita et al. | 606/200 |
| 5,911,734 A | 6/1999 | Tsugita et al. | 606/200 |
| 5,916,236 A | 6/1999 | Muijs Van de Moer et al. | 606/213 |
| 5,928,192 A | 7/1999 | Maahs | 604/96 |
| 5,928,260 A | 7/1999 | Chin et al. | 606/200 |
| 5,935,147 A | 8/1999 | Kensey et al. | 606/213 |
| 5,935,148 A | 8/1999 | Villar et al. | 606/213 |
| 5,941,249 A | 8/1999 | Maynard | 128/898 |
| 5,944,738 A | 8/1999 | Anplatz et al. | 606/213 |
| 5,947,997 A | 9/1999 | Pavcnik et al. | 606/213 |
| 5,951,589 A | 9/1999 | Epstein et al. | 606/213 |
| 5,954,694 A | 9/1999 | Sunseri | 604/96 |
| 5,957,940 A | 9/1999 | Tanner et al. | |
| 5,976,174 A | 11/1999 | Ruiz | 606/213 |
| 5,980,514 A | 11/1999 | Kupiecki et al. | 606/108 |
| 5,980,555 A | 11/1999 | Barbut et al. | 606/200 |
| 5,989,281 A | 11/1999 | Barbut et al. | 606/200 |
| 5,993,469 A | 11/1999 | McKenzie et al. | 606/159 |
| 5,997,557 A | 12/1999 | Barbut et al. | 606/159 |
| 6,007,523 A | 12/1999 | Mangosong | 604/284 |
| 6,007,557 A | 12/1999 | Ambrisco et al. | 606/200 |
| 6,010,517 A | 1/2000 | Baccaro | 606/151 |
| 6,010,522 A | 1/2000 | Barbut et al. | 606/200 |
| 6,024,754 A | 2/2000 | Engelson | 606/213 |
| 6,024,755 A | 2/2000 | Addis | 606/213 |
| 6,024,756 A | 2/2000 | Huebsch et al. | 606/213 |
| 6,027,520 A | 2/2000 | Tsugita et al. | 606/200 |
| 6,033,420 A | 3/2000 | Hahnen | 606/185 |
| 6,042,598 A | 3/2000 | Tsugita et al. | 606/200 |
| 6,048,331 A | 4/2000 | Tsugita et al. | 604/96 |
| 6,051,014 A | 4/2000 | Jang | 606/200 |
| 6,051,015 A | 4/2000 | Maahs | 606/200 |
| 6,056,720 A | 5/2000 | Morse | 604/96 |
| 6,068,621 A | 5/2000 | Balceta et al. | 604/500 |
| 6,074,357 A | 6/2000 | Kaganov et al. | 604/8 |
| 6,079,414 A | 6/2000 | Roth | 128/898 |
| 6,080,182 A | 6/2000 | Shaw et al. | 606/213 |
| 6,080,183 A | 6/2000 | Tsugita et al. | 606/213 |
| 6,083,239 A | 7/2000 | Addis | 606/200 |
| 6,132,438 A | 10/2000 | Fleischman et al. | 606/139 |
| 6,136,016 A | 10/2000 | Barbut et al. | 606/200 |
| 6,139,527 A | 10/2000 | Laufer et al. | 604/114 |
| 6,152,144 A | 11/2000 | Lesh et al. | 128/898 |
| 6,161,543 A | 12/2000 | Cox et al. | 128/898 |
| 6,231,544 B1 * | 5/2001 | Tsugita et al. | 604/104 |
| 6,231,561 B1 | 5/2001 | Frazier et al. | 604/500 |
| 6,231,589 B1 | 5/2001 | Wessman et al. | 606/200 |
| 6,235,044 B1 * | 5/2001 | Root et al. | 606/200 |

| | | | |
|---|---|---|---|
| 6,267,760 B1 | 7/2001 | Swanson | 606/49 |
| 6,328,757 B1 * | 12/2001 | Matheny | 606/213 |
| 6,419,669 B1 * | 7/2002 | Frazier et al. | 604/500 |
| 6,551,303 B1 * | 4/2003 | Van Tassel et al. | 606/200 |
| 6,652,555 B1 | 11/2003 | Van Tassel et al. | |
| 6,652,556 B1 | 11/2003 | Van Tassel et al. | |
| 6,689,150 B1 | 2/2004 | Van Tassel et al. | |
| 2001/0039435 A1 | 11/2001 | Roue et al. | 606/216 |
| 2002/0022860 A1 | 2/2002 | Borillo et al. | |

FOREIGN PATENT DOCUMENTS

| | | |
|---|---|---|
| WO | WO 93/13712 | 7/1993 |
| WO | WO 97/21402 | 6/1997 |
| WO | WO 97/28749 | 8/1997 |
| WO | WO 98/02100 | 1/1998 |
| WO | WO 98/17187 | 4/1998 |
| WO | WO 98/23322 | 6/1998 |
| WO | WO 99/07289 | 2/1999 |
| WO | WO 99/08607 | 2/1999 |
| WO | WO 99/30640 | 6/1999 |
| WO | WO 00/27292 | 5/2000 |
| WO | WO 00/53120 | 9/2000 |
| WO | WO 01/21247 | 3/2001 |
| WO | WO 01/26726 | 4/2001 |
| WO | WO 01/30266 | 5/2001 |

OTHER PUBLICATIONS

Cragg, et al., "A New Percutaneous Vena Cava Filter", *ALJ*, 141: 601-604, Sep. 1983.

Sugita et al., "Nonsurgical Implantation of a Vascular Ring Prosthesis Using Thermal Shape Memory Ti/Ni Alloy (Nitinol Wire)," *Trans. Am. Soc. Artif. Intern. Organs*, vol. XXXII, 30-34, 1986.

Ruttenberg, Nonsurgical Therapy of Cardiac Disorders, *Pediatric Consult*, vol. 5, No. 2, pages not numbered, 1986.

Rashkind et al., "Nonsurgical Closure of patent ductus arteriosus: clinical application of the Rashkind PDA Occluder System," *Circulation* 75, No. 3, 583-592, 1987.

Lock et al., "Transcatheter Umbrella Closure of Congenital Heart Defects," *Circulation*, vol. 75, No. 3, 593-599, 1987.

Wessel, et al. "Outpatient Closure of the patent ductus arteriosus," *Circulation*, vol. 77, No. 5, 1068-1071, 1988.

Lock et al., "Transcatheter Closure of Atrial Septal Defects," *Circulation*, vol. 79, No. 5, 1091-1099, May 1989.

* cited by examiner

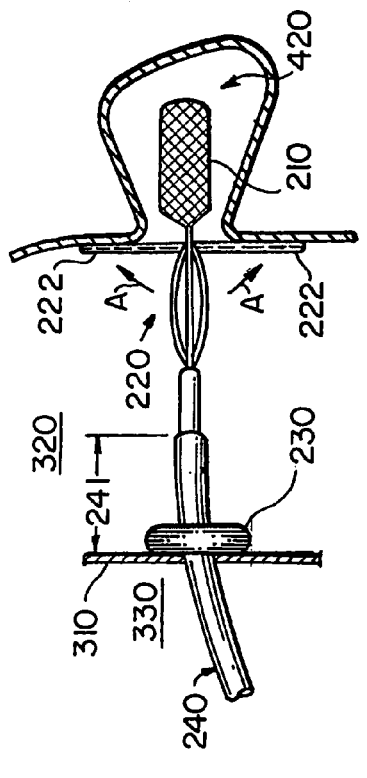
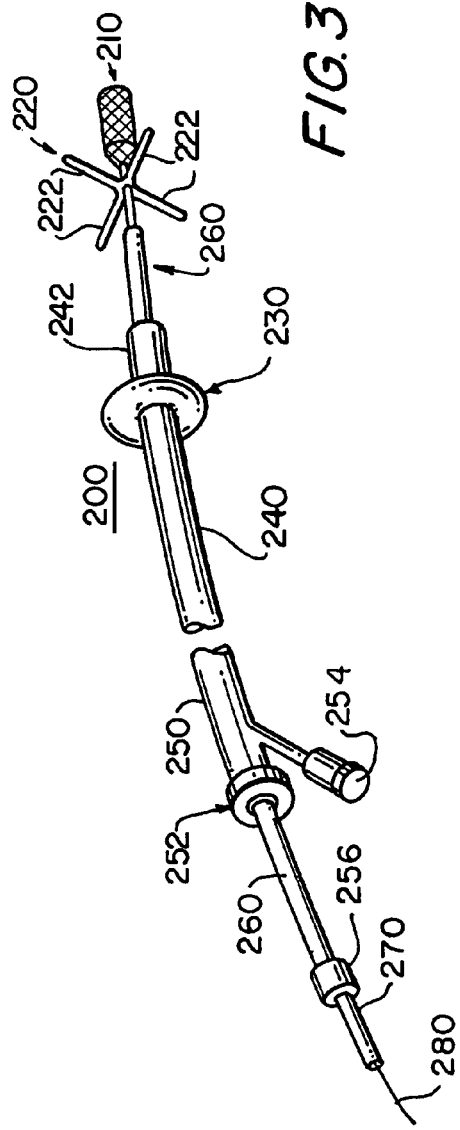
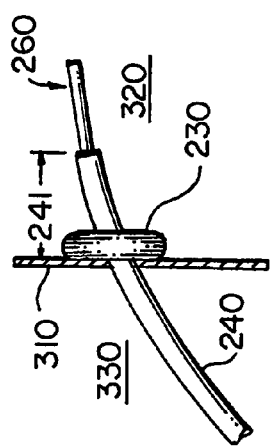
FIG. 3
FIG. 4
FIG. 5

APPARATUS FOR IMPLANTING DEVICES IN ATRIAL APPENDAGES

This application claims the benefit of U.S. provisional application No. 60/234,111, filed Sep. 21, 2000, which is hereby incorporated by reference in its entirety herein.

BACKGROUND OF THE INVENTION

1. Field of the Invention

The invention relates to apparatus for implanting devices in atrial appendages. The devices may be used to filter or otherwise modify blood flow between the atrial appendage and an associated atrium of the heart to prevent thrombi from escaping from the atrial appendage into the body's blood circulation system. In particular the invention relates to apparatus for percutaneous delivery and implantation of such devices.

2. Description of the Related Art

There are a number of heart diseases (e.g., coronary artery disease, mitral valve disease) that have various adverse effects on a patient's heart. An adverse effect of certain cardiac diseases, such as mitral valve disease, is atrial (or auricular) fibrillation. Atrial fibrillation leads to depressed cardiac output. A high incidence of thromboembolic (i.e., blood clot particulate) phenomena is associated with atrial fibrillation, and the left atrial appendage (LAA) is frequently the source of the emboli (particulates).

Thrombi (i.e., blood clots) formation in the LAA may be due to stasis within the fibrillating and inadequately emptying LAA. Blood pooling in the atrial appendage is conducive to the formation of blood clots. Blood clots may accumulate and build upon themselves. Small or large fragments of the blood clots may break off and propagate out from the atrial appendage into the atrium. The blood clot fragments can then enter the body's blood circulation and embolize distally into the blood stream.

Serious medical problems result from the migration of blood clot fragments from the atrial appendage into the body's blood stream. Blood from the left atrium and ventricle circulates to the heart muscle, the brain, and other body organs, supplying them with necessary oxygen and other nutrients. Emboli generated by blood clots formed in the left atrial appendage may block the arteries through which blood flows to a body organ. The blockage deprives the organ tissues of their normal blood flow and oxygen supply (ischemia), and depending on the body organ involved leads to ischemic events such as heart attacks (heart muscle ischemia) and strokes (brain tissue ischemia).

It is therefore important to treat cardiac conditions to prevent fragments or emboli generated by any blood clots that may have formed in the atrial appendages, from propagating through the blood stream to the heart muscle, brain or other body organs.

Some recently proposed methods of treatment are directed toward implanting a plug-type device in an atrial appendage to occlude the flow of blood therefrom.

A preventive treatment method for avoiding thromboembolic events (e.g., heart attacks, strokes, and other ischemic events) involves filtering out harmful emboli from the blood flowing out of atrial appendages. Co-pending and co-owned U.S. patent application Ser. No. 09/428,008, now U.S. Pat. No. 6,551,303; U.S. patent application Ser. No. 09/614,091, now U.S. Pat. No. 6,689,150; U.S. patent application Ser. No. 09/642,291, now U.S. Pat. No. 6,652,555; U.S. patent application Ser. No. 09/697,628, and now U.S. Pat. No. 6,652,556; and U.S. patent application Ser. No. 09/932,512, now published as U.S. Application Publication No. 20020022860A1, all of which are hereby incorporated by reference in their entireties herein, describe expandable filtering devices which may be implanted in an atrial appendage to filter the blood flow therefrom.

The implant devices in a compact state may be delivered to their atrial appendage situs percutaneously through femoral or jugular blood vessels using conventional catheterization apparatus. The position of an implanted device may be observed using common imaging techniques, for example, radiography or echocardiography. The implant devices are deployed by expanding them in situ. The devices are retained in position by expandable structures which engage surrounding atrial appendage tissue. The expandable structures may include tissue piercing anchors.

To function effectively the devices must be deployed from suitable positions within or about the atrial appendages. For example, the filter elements of a device must be correctly centered or positioned across an atrial appendage ostium for the device to properly intercept and filter blood flowing out of the atrial appendage. Placing a device in a suitable deployment position may require position probing or adjustment from an initial as-delivered position.

It would therefore be desirable to provide catheterization apparatus having positioning guides, which enable controlled position probing and readjustment of the initial as-delivered implant device position to place the device in a suitable deployment position in the atrial appendage.

Further, the implant procedures may include transseptal catheterization which involves puncturing an atrial septum and advancing an access sheath through the septum. The access sheath provides a conduit through which an implant device may be delivered across the septum into the adjoining atrium. Inadvertent movement of the sheath during the catheterization procedure may lead to undesirable medical complications. For example, retrograde slippage may cause the sheath to disengage from the septum, which in turn may necessitate repeated puncturing or crossing of the septum to regain access to the adjoining atrium. Further, instability in the position or orientation of the access sheath may make the delivery of a device for placement in an appendage geometrically difficult.

It would therefore also be desirable to provide transseptal catheterization apparatuses which include securement devices for restraining the movement of and securing the position of the access sheath traversing the septum.

SUMMARY OF THE INVENTION

The invention provides a catheterization apparatus having a positioning device or guide, which enables controlled position probing and readjustment of the initial as-delivered implant device position. The catheterization apparatus may include one or more nested tubes, wires or shafts. The positioning guide may be attached to a positioning tube passing through the catheter apparatus. Using the positioning guide, the implant device position in the atrial appendage may be readjusted from the as-delivered position to a desired deployment position.

The positioning guide may have an expandable structure. The structure may be expandable from a compact state to an expanded state. The positioning guide is delivered in its compact state to a location adjoining the ostium of an atrial appendage. The apparatus may include size-adjusting mechanisms for expanding the positioning guide in situ. The positioning guide may be deployed by expanding it to engage or contact portions of the atrial wall proximate to the ostium for mechanical support. The deployed guide thereby holds and stabilizes outer portions of the catheter apparatus in a fixed position. An implant device attached to a shaft passing through the catheterization apparatus may then be reversibly positioned within the atrial appendage. The implant device position may be monitored, for example, by echocardiography, radiography or fluoroscopy. After the implant device is suitably positioned and deployed, the positioning guide may be contracted to its compact non-expanded state and retracted.

In an embodiment of the catheterization apparatus which may be useful for transseptal catheterization, a securement means is attached to an access sheath in the catheterization apparatus. The access sheath is used to puncture an atrial septum and then advanced through the puncture to provide a passage way through which an implant device may be delivered to an adjoining atrium. The securing means may, for example, include an inflatable disk having an inflated diameter that is larger than the size of the septal puncture. The inflatable disk may be deployed to engage distal surfaces of the punctured septum to secure the position of the access sheath relative to the septum.

Other embodiments of the positioning guides (and securement means) may have other kinds of inflatable or expandable structures which allow the positioning devices (and securement means) to have compact sizes for delivery and which can later be enlarged in situ.

Further features of the invention, its nature, and various advantages will be more apparent from the accompanying drawing and the following detailed description.

BRIEF DESCRIPTION OF THE DRAWINGS

FIG. 3 is a schematic view of a portion of a transseptal catheterization apparatus having a positioning guide for reversible or adjustable placement of an implant device in an atrial appendage, and a securement means for restraining movement of a septum-traversing access sheath in accordance with the principles of the invention.

FIG. 4 is a schematic view of a portion of the transseptal catheterization apparatus of FIG. 3 illustrating the deployment of the securement means to restrain movement of a septum-traversing sheath in accordance with the principles of the invention.

FIG. 5 is a schematic view of a portion of the transseptal catheterization apparatus of FIG. 3 illustrating figuratively the deployment of the positioning guide to engage atrial wall surfaces proximate to the ostium of an atrial appendage in accordance with the principles of the invention.

DESCRIPTION OF THE PREFERRED EMBODIMENTS

Implant devices for filtering or otherwise modifying blood flow between an atrial appendage and its atrium may be attached to a catheter shaft and then be percutaneously delivered to the appendage through a blood vessel leading to the heart.

Figure 1:
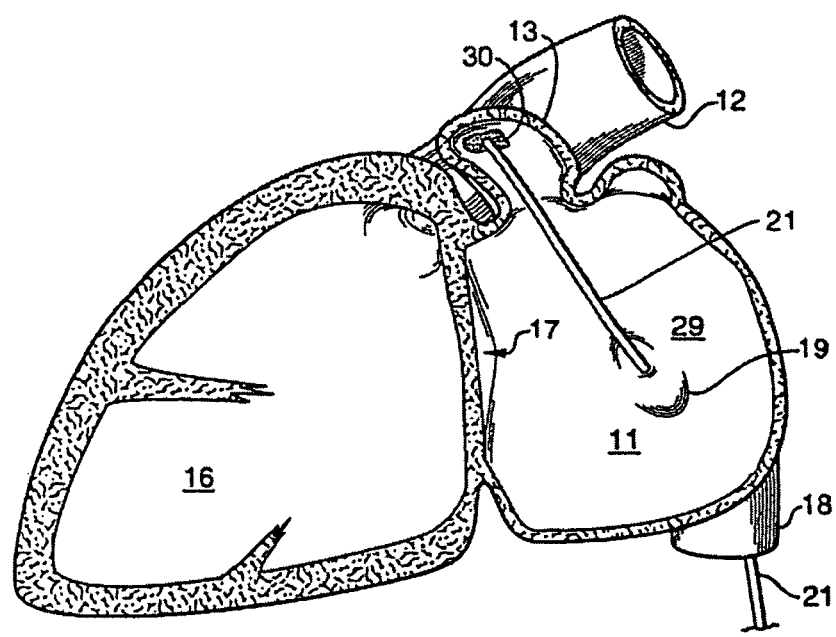
FIG. 1 is a partial cross sectional view of a heart illustrating a conventional catheter entering a left atrial appendage using a transseptal procedure.

FIG. 1 illustrates, for example, catheter 21 inserted through a femoral vein (not shown) entering the right atrium of the heart through the inferior vena cava 18, and then passing into left atrium 11 through the fossa ovalis 19 or through the septum 29 before entering the left atrial appendage 13. Alternatively (not shown in FIG. 1), catheter 21 may enter the left ventricle 16 of the heart through the aorta 12, and then pass through mitral valve 17 to reach left atrial appendage 13. An implant device (not shown) attached to catheter 21 may be used to prevent thrombus 30 or emboli generated therefrom from migrating into atrium 11. The device may include materials having suitable properties (e.g., radio-opacity) that make it possible to monitor the in-vivo device position during and after the catheterization position using external imaging techniques such as radiography or fluoroscopy, echocardiography, and ultrasound.

The present invention provides a catheterization apparatus having a positioning device or guide, which enables controlled position probing and readjustment of an initial as-delivered implant device position. The implant device position in the atrial appendage may be readjusted from the as-delivered position to a desired deployment position. The catheterization apparatus may include one or more nested tubes, wires or shafts. The positioning guide may be attached to a positioning tube passing through the catheter apparatus.

The positioning guide may have an expandable or inflatable structure designed to engage (contact) atrial wall portions surrounding the ostium. The structure may be designed to be reversibly expandable from a compact state suitable for percutaneous delivery and withdrawal. Further, the positioning guide may be designed to engage surrounding atrial wall portions to provide a stable and reproducible pathway for movement of a device-carrying shaft in and out of the atrial appendage.

The positioning guide may be made of suitable biocompatible materials including metals and polymeric materials such as ePFTE (e.g., Gortex®), polyester (e.g., Dacron®), PTFE (e.g., Teflon®), stainless steel and shape-memory alloys (e.g., nitinol) fibers or wires.

Figure 2C:
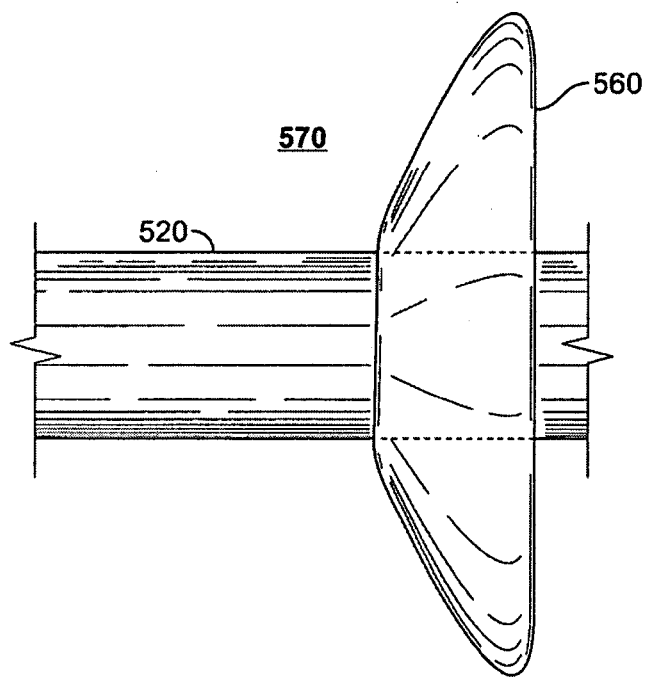
FIGS. 2a and 2b illustrate examples of wire patterns or configurations of expanded positioning guides in accordance with the principles of the invention FIG. 2c schematically illustrates an inflatable balloon-type positioning guide in accordance with the principles of the invention.
Figure 2A:
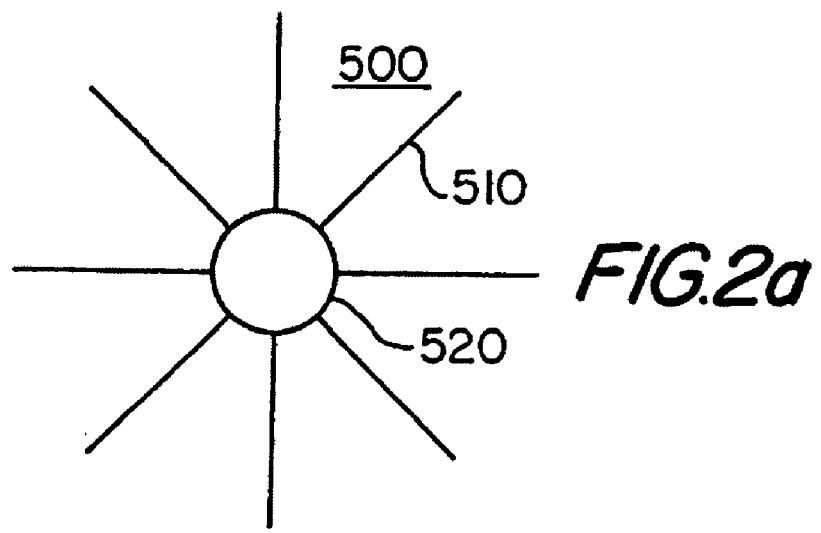
Figure 2B:
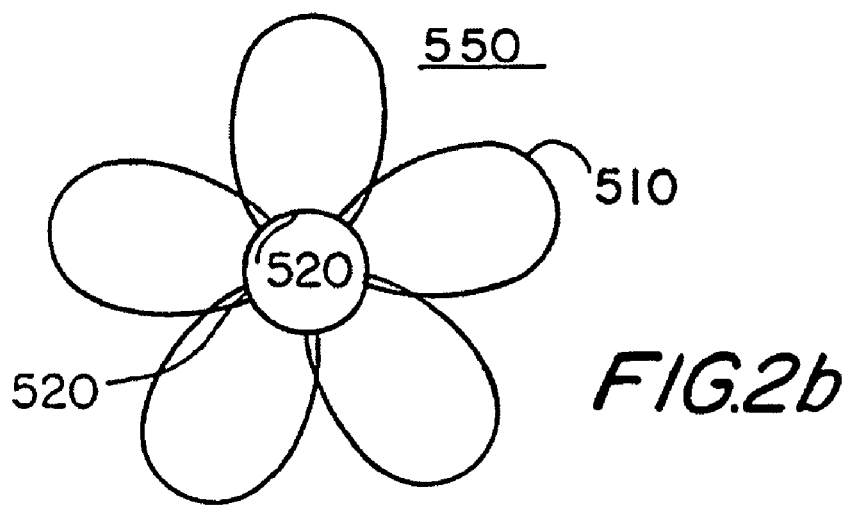

Positioning guides according to one embodiment may be formed from lengths of wires. The wires may be made of suitable elastic materials including shape memory alloy materials such as nitinol. There may be one or more wires or wire configurations which make up the positioning guide. In the compact state of the positioning guide that is suitable for percutaneous delivery, the wires may lie substantially along the positioning tube. The wires or wire configurations made, for example, from shape-memory alloy materials, may have preformed shapes. In the expanded state of the positioning guides, these wires may revert to their preformed shapes in which they may extend away from the positioning tube. The extended wires may have any suitable configuration for engaging the atrial wall portions. For example, the extended wires may have a straight spoke-like pattern or have more complex patterns such as overlapping arcuate patterns. FIG. 2a illustrates, for example, a spoke-like configuration of wires 510 in the expanded or deployed state of a positioning guide 500. Wires 510 extend radially outward away from positioning tube 520 on which guide 500 is disposed. Further, for example, FIG. 2b illustrates an overlapping arcuate pattern of wires 510 in the expanded or deployed state of positioning guide 550.

The catheterization apparatus may include suitable size-adjusting mechanisms that allow the positioning guide to be reversibly expanded in situ. For example, the apparatus may include a retractable sleeve which covers and holds the elastic or shape-memory alloy wires forming a positioning guide in a compact configuration along or in close proximity to the positioning tube. The positioning guide may be deployed by retracting the sleeve to allow the wires to expand or unfurl radially outward. The sleeve may be moved forward to reverse the expansion as needed to return the positioning guide to its compact state. Alternatively, the wires may be contained within the delivery tube, and attached, for example, to a sliding push rod that enables the wires to be retractably extended through small diameter openings or holes in the delivery tube walls.

The positioning guide in its non-expanded compact state is delivered to a location adjoining the ostium of an atrial appendage. The positioning guide is deployed by expanding it to engage or contact portions of the atrial wall proximate to the ostium for mechanical support. The outermost engagement points may be separated by distances that are larger than the positioning tube diameter. Preferably, the separation distances are several times larger than the positioning tube diameter to obtain a support configuration having a wide geometry that favors mechanical stability. Additionally, the position guide may be suitably advanced forward to bear upon the atrial wall portions with a contact pressure adequate to generate frictional resistance to its lateral movement. Thus, the deployed positioning guide may mechanically hold and stabilize the positioning tube in a fixed position relative to the ostium. An implant device attached to a shaft passing through the positioning tube may then be reversibly placed at a location within the atrial appendage. The implant device position may be monitored, for example, by electrocardiographic, radiographic, or fluoroscopic imaging. After the implant device is suitably positioned or deployed, the positioning guide may be contracted and retracted.

Other embodiments of the positioning guides may have other kinds of inflatable or expandable structures which allow the positioning guides to have compact sizes for delivery and which can later be enlarged in situ. For example, positioning guides according to one of these other embodiments may have inflatable balloon-type structures. The balloons may be made of suitable elastic membranes, for example, made of urethane or silicone material. FIG. 2c schematically illustrates, for example, a balloon-type structure 560 of a positioning guide 570.

An embodiment of a catheterization apparatus may be useful for transseptal catheterization. The apparatus of this embodiment has an access sheath which is used to provide a conduit or pathway for device delivery across a septum between adjoining atriums. The apparatus includes a securement means which may be used to restrain movement of the septum-traversing access sheath. The securement means is disposed on or about the distal end of the access sheath.

The access sheath may be an outermost tube of the catheterization apparatus. Known catheterization techniques may be used to have the access sheath penetrate and traverse a septum. A known technique, for example, uses a conventional dilator (obturator) device having a covered needle in its tip. The dilator is preloaded in the access sheath such that the dilator tip extends out of the distal end of the access sheath. The preloaded access sheath is advanced into an atrium through the body's vasculature. Next, the dilator needle is advanced through the dilator tip to puncture the atrial septum, following which the dilator itself is advanced to dilate the puncture opening. The access sheath is then advanced through the dilated puncture opening across the septum into the adjoining atrium. Finally, the dilator device is then withdrawn from the access sheath.

The securement means in the catheterization apparatus of the present invention may be deployed to restrain further movement of the septum-traversing access sheath. The securing means may, for example, include an inflatable disk having an inflated diameter that is larger than that size of the septal puncture or the diameter of the access tube. Preferably, the inflated diameter is several times larger than the diameter of the access tube. In catheterization apparatus useful for procedures on adult hearts, the inflated diameter may, for example, be in the range of about 5 to 10 mm. The inflatable disk may be fabricated from membranes made of bicompatible materials such as silicone, urethane, or other biocompatible polymers.

The catheterization apparatus may include suitable means for reversibly inflating the securement means. For example, the access sheath may include a tube connected to the inflatable disk structure through which pressurizing fluids may be supplied to inflate the disk. The inflatable disk may be deployed to engage the distal surfaces of the punctured septum to secure the position of the access sheath relative to the septum and to restrain inadvertent movement of the access sheath.

Other embodiments of the securement means may have other kinds of inflatable or expandable structures which allow the securement means to have compact sizes for delivery and which can later be enlarged in situ.

FIG. 3 illustrates, for example, transseptal catheterization apparatus 200 having a positioning guide 220 for reversible placement of an implant device 210 in an atrial appendage, and a securement means 230 for restraining inadvertent or uncontrolled movement of a septum-traversing access sheath 240.

Apparatus 200 includes coaxially nested access sheath 240, delivery tube 260, positioning tube 270, and device shaft 280, all of which are connected to or pass through handle manifold 250.

Access sheath 240 may form an outer tubular structure of catheterization apparatus 200. Rigid biocompatible tube materials such as metals and plastics may be used to fabricate access sheath 240. However, access sheath 240 may be sufficiently flexible for it to course through blood vessels leading to the heart. Access sheath 240 may have an outer diameter at distal end 242 suitable for percutaneous passage to the heart through readily accessible blood vessels, for example, the femoral veins.

One end (proximal end) of access sheath 240 is attached to handle manifold 250. Inflatable securement means 230 is disposed on or built into access sheath 240 toward its distal end. Securement means 230 may be reversibly inflated, for example, by pressurizing fluids injected through inflation port 254 disposed on manifold 250.

Handle manifold 250 includes fluid seal structure 252 through which a delivery tube 260 passes through and retractably extends into access sheath 240. Fluid seal 252 may be any conventional seal designed to prevent leakage of fluids while delivery tube 260 is retracted or extended into access sheath 240. Fluid seal 252 may, for example, be a conventional hemostatic seal. Rigid biocompatible tube materials such as metals and plastics similar to those used to fabricate access sheath 240 also may be used to fabricate delivery tube 260. Delivery tube 260 may have sufficient flexibility for it to course through access sheath 240 in the latter's deployed position through blood vessels leading to the heart. Delivery tube 260 may have an outer diameter sized to allow its smooth movement within access sheath 240. The outer diameter of delivery tube 260 also may be sufficiently smaller than the inner diameter of access sheath 240 to allow pressurizing fluids to flow between securement means 230 and inflation port 254. Alternatively or additionally, the outer surface of delivery tube 260 may be grooved to provide flow channels for pressurizing fluids to flow between securement means 230 and inflation port 254.

The inner diameter of delivery tube 260 is sized to be sufficiently large to accept and allow passage of positioning guide 220 disposed on the distal end of a positioning tube 270. Rigid biocompatible tube materials such as metals and plastics similar to those used to fabricate access sheath 240 and delivery tube 260 also may be used to fabricate positioning tube 270. Positioning tube 270 may be sufficiently flexible for it to course through delivery tube 260 in the latter's deployed position through access sheath 240. Positioning tube 270 retractably extends into delivery tube 260 through seal 256 disposed on the proximal end of delivery tube 260. Seal 256 is designed to prevent fluid leakage, and may, for example, be of a type similar to fluid seal 252.

Positioning guide 220 disposed on the distal end of positioning tube 270 may have a compact state from which it may be reversibly expanded to an expanded state. FIG. 3 shows for purposes of illustration an exemplary positioning guide 220 in its expanded state. Expanded positioning guide 220 has a structural configuration with four extended fingers 222 suitable for engaging or contacting atrial walls for mechanical support to stabilize the position of positioning tube 270. The four extended fingers shown in FIG. 3 have a size which substantially larger than the diameter of delivery tube 260. However, it will be understood that positioning guide 220 is passable through delivery tube 260 only when the former is in its compact retracted state. Positioning tube 270 may include means such as a trip wire, a push rod, a retractable sleeve, or other suitable means to reversibly deploy positioning guide 220. Positioning tube 270 itself may, for example, serve as a push rod, in which case positioning guide 220 may be expanded or contracted by respectively advancing or retracting positioning tube 270 through delivery tube 260.

The inner diameter of positioning tube 270 is sized to be sufficiently large to accept and allow passage of compacted implant device 210 attached to one end of a device shaft 280. Implant device 210 may, for example, be any one of the self-expanding or inflatable filtering devices disclosed U.S. patent application Ser. No. 09/428,008, now U.S. Pat. No. 6,551,303; U.S. patent application Ser. No. 09/614,091, now U.S. Pat. No. 6,689,150; U.S. patent application Ser. No. 09/642,291, now U.S. Pat. No. 6,652,555; U.S. patent application Ser. No. 09/697,628, now U.S. Pat. No. 6,652,556; and U.S. patent application Ser. No. 09/932,512, now published as U.S. Application Publication No. 20020022860A1, all of which are hereby incorporated by reference herein. Device shaft 280 may be a conventional catheter shaft having conventional fixtures for device attachment. Device shaft 280 may, for example, have a solid or tubular structure made of solid metals, metal braids, solid polymers, polymer braids, or any suitable combination thereof. Shaft 280 may enclose other tubes or structures that may be required for device deployment. For example, device shaft 280 may include some lumen for supplying fluids for inflation of an expandable balloon in a balloon-inflatable type of device 210.

Catheterization apparatus 200 (or other embodiments thereof) may be used to controllably and adjustably place an implant device at a suitable deployment location within an atrial appendage. Position guide 220 and/or securement means 230 may be used to provide a mechanically stable pathway for delivery of the device, and for adjusting the device location within the atrial appendage before device deployment.

With reference to FIG. 4, in a transseptal catheterization procedure, access sheath 240 with securement means 230 in its compact state is introduced into a right atrium 330 through the body's vasculature. The progress of access sheath 240 through the body may be monitored, for example, by echocardiography, radiographic or fluoroscopic imaging. A conventional needle and dilator assembly (not shown) reversibly sliding through access sheath 240 may be used to puncture and dilate septum 310. Access sheath 240 is advanced forward through the dilated puncture opening in septum 310. A distal length 241 of access sheath 240 is advanced across septum 310 into left atrium 320. After securement means 230 disposed on the distal end of access sheath 240 advances across septum 310, forward advancing motion of access sheath 240 may be halted. Securement means 230 may then be deployed, for example, by injecting pressurizing fluid through inflation port 254. With securement means 230 inflated movement of access sheath 240 is restrained by engagement of means 230 with distal wall surfaces of septum 310. This engagement may prevent retrograde movement or slippage of access sheath 300 that may occur inadvertently, or for example, in mechanical reaction to the action of advancing other strictures such as a tight fitting delivery tube 260 through access sheath 230. FIG. 4 shows access sheath 240 with length 241 jutting into left atrium 320 secured against septum 310 by inflated securement means 230, and providing a mechanically stable conduit for delivery tube 260 to access left atrium 320.

Implant device 210 and other catheter structures including positioning guide 220 may be passed through delivery tube 260 into left atrium 320. FIG. 5 figuratively illustrates the deployment of the positioning guide 220 to engage atrial wall surfaces 430 proximate to the ostium 410 of a left atrial appendage 420 for mechanical support.

After access sheath 240 is secured against septum 310 by inflated securement means 230, and delivery tube 260 is introduced into left atrium 320, positioning tube 270 with positioning guide 220 in its compact state is advanced through delivery tube 260 into left atrium 320. Positioning tube 270 is advanced sufficiently into left atrium 320 so that positioning guide 220 butts up against or is very close to ostium 410. Positioning guide 220 is then deployed so that it engages surface portions of the atrial wall 430 surrounding ostium 410. In FIG. 5, directions A figuratively depict the motion of fingers 222 during the deployment of guide 220. During the deployment fingers 222 move from a contracted configuration alongside positioning tube 270 to an expanded configuration with fingers 222 spread radially outward Fingers 222 in the expanded configuration engage atrial wall 430 for mechanical support. By engaging or contacting atrial wall 430 positioning guide 220 mechanically stabilizes the position of tubes 260 and 270 relative to that of atrial appendage 420. Implant device 210 attached to shaft 280 may be delivered to a location within atrial appendage 420 simultaneously with the delivery of positioning guide 220 to a location butting up against or very close to ostium 410. Alternatively, implant device 210 may be delivered after positioning guide 220 has been deployed to engage atrial walls 430 for mechanical support. The location of device 210 may be adjusted by sliding shaft 280 through the stabilized pathway provided by positioning tube 270 held in relatively fixed position by deployed positioning guide 220.

It will be understood that the foregoing is only illustrative of the principles of the invention, and that various modifications can be made by those skilled in the art without departing from the scope and spirit of the invention. It will be understood that terms like "distal" and "proximal", and other directional or orientational terms are used herein only for convenience, and that no fixed or absolute orientations are intended by the use of these terms.

What is claimed is:

1. A method for implanting a device in an atrial appendage, said method comprising:
   providing a catheterization apparatus comprising:
   a tube assembly for providing a passageway for movement of said device through vasculature to said atrial appendage, said assembly comprising at least:
   an outer tube;
   a shaft for transporting said device through said assembly; and
   a positioning guide for engaging at least a portion of an atrial wall for mechanical support of portions of said assembly;
   percutaneously advancing said tube assembly through a blood vessel to establish a passageway to an atrium;
   introducing said positioning guide to a location near an ostium of said atrial appendage;
   deploying said positioning guide to engage said portion of an atrial wall for mechanical support;
   using said shaft to transport said device through said passageway to a position within said atrial appendage; and
   releasing said device.

2. The method of claim 1 wherein said providing a catheterization apparatus comprises providing a positioning guide that is disposed on a positioning tube that retractably extends through said outer tube.

3. The method of claim 2 wherein said providing a positioning guide comprises providing a positioning guide having a reversibly expandable structure.

4. The method of claim 3 wherein said providing a positioning guide having a reversibly expandable structure comprises providing a positioning guide having at least a preformed wire configuration.

5. The method of claim 3 wherein said providing a positioning guide having a reversibly expandable structure comprises providing a positioning guide having an inflatable balloon.

6. The method of claim 5 wherein said providing a catheterization apparatus comprises providing a lumen for supplying pressurizing fluids to inflate said inflatable balloon.

7. The method of claim 1 wherein:
   said providing a catheterization apparatus comprises providing a delivery tube for advancing said positioning guide through said tube assembly to a location proximate to said appendage; and
   said delivery tube retractably extends through said outer tube.

8. The method of claim 7 wherein:
   said providing a catheterization apparatus further comprises providing a positioning tube that retractably extends through said delivery tube; and
   said positioning guide is disposed on an end of said positioning tube.

9. The method of claim 1 wherein said providing, a catheterization apparatus comprises providing a securement means having a reversibly expandable structure.

10. The method of claim 9 wherein said providing a catheterization apparatus further comprises providing a securement means having an inflatable structure made from an elastic membrane.

11. The method of claim 10 wherein said deploying comprises inflating said inflatable structure.

12. The method of claim 9 wherein said deploying comprises expanding said reversibly expandable structure.

13. The method of claim 1 wherein:
   providing said tube assembly further comprises providing a securement means disposed on an end of said outer tube; and
   said securement means engages surface portions of a septum traversed by said outer tube to restrain further movement of said outer tube.

* * * * *